(12) United States Patent
Watanabe et al.

(10) Patent No.: US 8,937,253 B2
(45) Date of Patent: Jan. 20, 2015

(54) CATHETER WIRE

(71) Applicant: Hitachi Cable, Ltd., Tokyo (JP)

(72) Inventors: Takanobu Watanabe, Hitachi (JP);
Detian Huang, Hitachi (JP)

(73) Assignee: Hitachi Metals, Ltd., Tokyo (JP)

( * ) Notice: Subject to any disclaimer, the term of this patent is extended or adjusted under 35 U.S.C. 154(b) by 0 days.

(21) Appl. No.: 13/890,651

(22) Filed: May 9, 2013

(65) Prior Publication Data

US 2014/0236125 A1  Aug. 21, 2014

(30) Foreign Application Priority Data

Feb. 15, 2013  (JP) .................................. 2013-027818

(51) Int. Cl.
*H01B 7/18* (2006.01)
*A61M 25/09* (2006.01)

(52) U.S. Cl.
CPC .............................. *A61M 25/09033* (2013.01)
USPC .......................................... 174/107; 600/140

(58) Field of Classification Search
USPC ......... 174/107, 128.1; 385/111; 600/110, 140
See application file for complete search history.

(56) References Cited

U.S. PATENT DOCUMENTS

| | | | |
|---|---|---|---|
| 5,158,086 A * | 10/1992 | Brown et al. ................... | 600/459 |
| 5,751,879 A * | 5/1998 | Graham et al. ................ | 385/103 |
| 5,897,504 A * | 4/1999 | Buck et al. ..................... | 600/463 |
| 5,905,834 A * | 5/1999 | Anderson et al. .............. | 385/111 |
| 8,143,517 B2 | 3/2012 | Detian et al. | |
| 2002/0066503 A1* | 6/2002 | Matsui et al. .................. | 148/432 |
| 2004/0179795 A1* | 9/2004 | Cottevieille et al. ........... | 385/103 |
| 2004/0187977 A1* | 9/2004 | Matsui et al. .................. | 148/553 |
| 2007/0187134 A1* | 8/2007 | Detian et al. .................. | 174/126.1 |
| 2009/0076449 A1* | 3/2009 | Geis et al. .................. | 604/103.05 |
| 2009/0223713 A1* | 9/2009 | Detian et al. .................. | 174/99 R |
| 2010/0059247 A1* | 3/2010 | de Oliveira Lima et al. . | 174/103 |
| 2010/0116541 A1* | 5/2010 | Eshima .......................... | 174/388 |
| 2012/0015124 A1* | 1/2012 | Kitahara et al. .............. | 428/36.9 |
| 2012/0228024 A1* | 9/2012 | Omori et al. .................. | 174/72 A |
| 2012/0292079 A1* | 11/2012 | Muramatsu et al. ....... | 174/113 R |
| 2013/0133775 A1* | 5/2013 | Duncan et al. ................ | 138/129 |
| 2013/0319724 A1* | 12/2013 | Watanabe et al. ............ | 174/108 |

\* cited by examiner

*Primary Examiner* — Nicholas Lucchesi
*Assistant Examiner* — Gerald Landry, II
(74) *Attorney, Agent, or Firm* — Scully, Scott, Murphy & Presser, PC

(57) ABSTRACT

A catheter wire includes a core bundle formed by twisting a plurality of core wires each including a solid conductor covered with an insulation, a tape layer formed by spirally winding a binding tape on an outer periphery of the core bundle, a shield layer formed by spirally winding a metal wire on an outer periphery of the tape layer, and a sheath layer formed on an outer periphery of the shield layer. The binding tape is wound in a direction opposite to a twisting direction of the core wires. The solid conductor and the metal wire have a tensile strength of not less than 900 MPa and an elongation percentage of not more than 2%.

5 Claims, 2 Drawing Sheets

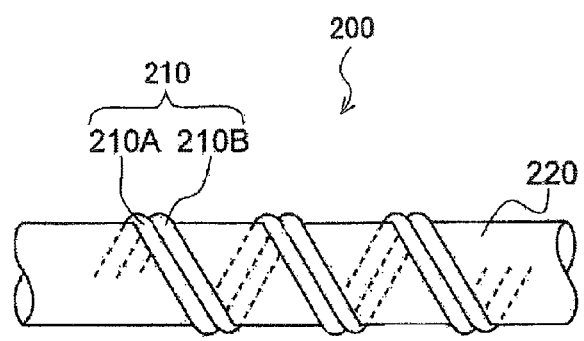
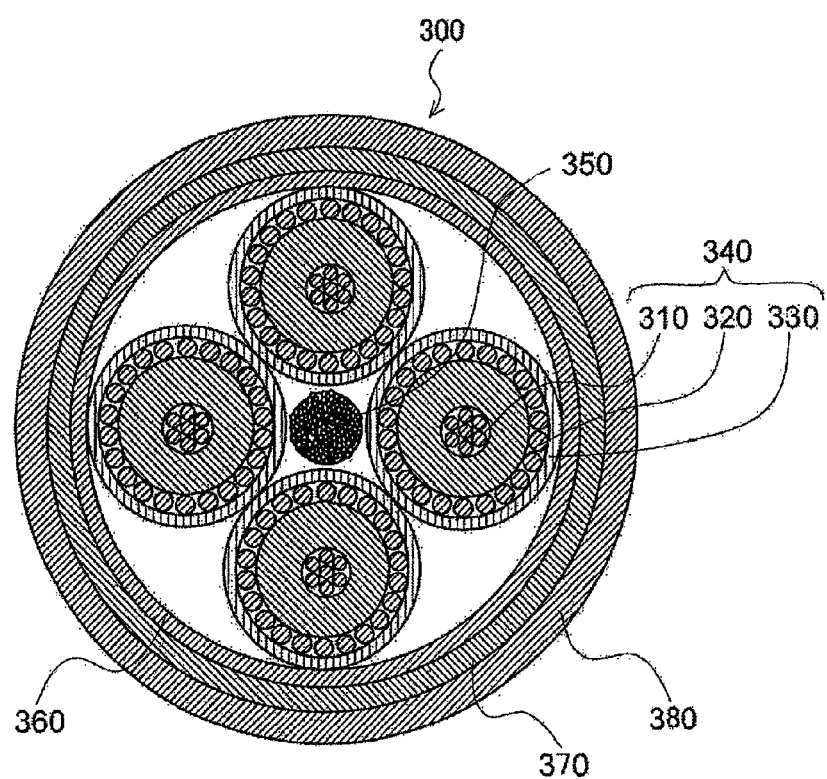

CATHETER WIRE

The present application is based on Japanese patent application No. 2013-027818 filed on Feb. 15, 2013, the entire contents of which are incorporated herein by reference.

BACKGROUND OF THE INVENTION

1. Field of the Invention

The invention relates to a catheter wire and, in particular, to a catheter wire that is to be equipped with an ultrasonic transducer and is good in a straight-advancing property and electrical characteristics in a bent state while a diameter thereof is reduced.

2. Description of the Related Art

As shown in FIG. 2, a conventional catheter wire is formed by twisting plural (seven in the illustrated example) enamel wires 100 in each of which a copper-alloy wire 110 is covered with a coating layer 120 formed of polyimide.

Meanwhile, a twisted wire 200 as shown in FIG. 3 is also known, in which a signal wire 210A and a ground wire 210B as a pair of insulated wires 210 each formed by covering a copper alloy twisted wire with an insulation are wound around an outer periphery of a central conductor wire 220 at a predetermined pitch.

Furthermore, a multicore cable 300 as shown in FIG. 4 is also known, in which coaxial cables 340 are twisted together around an outer periphery of a tension member 350 to form a core bundle, a binding tape 360 is wound around the core bundle and a shield layer 370 and a sheath 380 are further provided thereon. Each coaxial cable 340 is composed of an extra-fine insulated wire 310 formed by covering an inner conductor with an insulation, a conductor wire 320 wound therearound and a jacket layer 330 covering the conductor wire 320.

Such a catheter wire is disclosed in, e.g., U.S. Pat. No. 8,143,517.

SUMMARY OF THE INVENTION

Here, the structure shown in FIG. 2 in which the enamel wires 100 are twisted together does not have a shield layer and thus has a problem of unstable electrical characteristics. In addition, it is necessary to dissolve and remove the coating layer 120 using a chemical for connecting an ultrasonic transducer and this causes a problem of deterioration in processability or workability at the time of terminal processing.

Meanwhile, the twisted wire 200 shown in FIG. 3 has a problem of unstable electrical characteristics since the signal wire 210A is separated from the ground wire 210B when the twisted wire 200 is bent in a catheter.

In addition, in the multicore cable 300 shown in FIG. 4, the coaxial cable 340 constituting the core bundle is thick (e.g., 0.2 mm) and this causes a problem in that the overall outer diameter is difficult to be reduced to not more than 0.3 mm which is preferable as an intravascular catheter. Furthermore, if a diameter of the inner conductor of the extra-fine insulated wire 310 is reduced for the purpose of reduction in a diameter, conductor resistance increases and this may cause deterioration of electrical characteristics.

It is an object of the invention to provide a catheter wire that is to be equipped with an ultrasonic transducer and is good in a straight-advancing property and electrical characteristics in a bent state while a diameter thereof is reduced.

(1) According to one embodiment of the invention, a catheter wire comprises:

a core bundle formed by twisting a plurality of core wires each comprising a solid conductor covered with an insulation;

a tape layer formed by spirally winding a binding tape on an outer periphery of the core bundle;

a shield layer formed by spirally winding a metal wire on an outer periphery of the tape layer; and a sheath layer formed on an outer periphery of the shield layer, wherein the binding tape is wound in a direction opposite to a twisting direction of the core wires, and wherein the solid conductor and the metal wire have a tensile strength of not less than 900 MPa and an elongation percentage of not more than 2%.

In the above embodiment (1) of the invention, the following modifications and changes can be made.

(i) The solid conductor and the metal wire have a conductivity of not less than 80%.

(ii) A ratio (P/PD) of a twisting pitch (P) of the core wire to a twisted wire outer diameter (PD) is in a range of 15 to 25.

(iii) The sheath layer comprises a fluorine resin having a melt flow rate (MFR) of not less than 35.

(iv) The metal wire is wound in a same direction as the twisting direction of the core wires.

(v) The metal wire comprises a silver-plated wire.

EFFECTS OF THE INVENTION

According to one embodiment of the invention, a catheter wire can be provided that is to be equipped with an ultrasonic transducer and is good in a straight-advancing property and electrical characteristics in a bent state while a diameter thereof is reduced.

BRIEF DESCRIPTION OF THE DRAWINGS

Next, the present invention will be explained in more detail in conjunction with appended drawings, wherein:

FIG. 3 is a schematic cross sectional view showing a conventional twisted wire; and FIG. 4 is a schematic cross sectional view showing a conventional multicore cable.

DETAILED DESCRIPTION OF THE PREFERRED EMBODIMENTS

A catheter wire with ultrasonic transducer in the embodiment of the invention will be described below in conjunction with the drawings.

Figure 1:
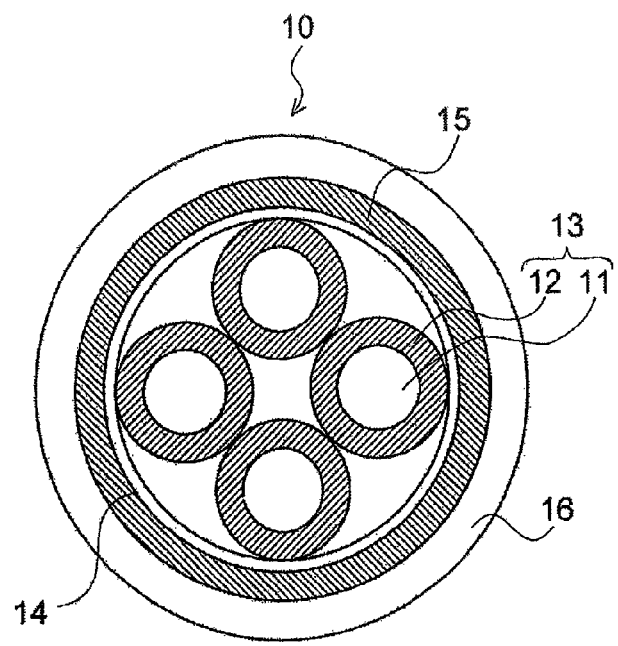
FIG. 1 is a schematic cross sectional view showing a catheter wire with ultrasonic transducer in an embodiment of the present invention.

As shown in FIG. 1, a catheter wire with ultrasonic transducer (hereinafter, referred to as "catheter wire") 10 has a core bundle formed by twisting plural core wires 13 each having a solid conductor 11 covered with an insulation 12, a tape layer 14 formed by spirally winding a binding tape around an outer periphery of the core bundle, a shield layer 15 formed by spirally winding a metal wire around an outer periphery of the tape layer 14, and a sheath layer 16 covering an outer periphery of the shield layer 15.

The solid conductor 11 is formed of a metal excellent in conductivity, e.g., copper or copper alloy, etc., and has a tensile strength of not less than 900 MPa and an elongation percentage of not more than 2%. This provides adequate elasticity to the catheter wire 10, and a straight-advancing property of a catheter (not shown) in a blood vessel is thus improved. Meanwhile, the solid conductor 11 has a conductivity of not less than 80%. This decreases a signal attenuation rate and it is thus possible to obtain good electrical characteristics.

The insulation 12 is formed of a fluorine resin having low-dielectric constant, e.g., tetrafluoroethylene perfluoroalkyl vinyl ether copolymer (PFA) or tetrafluoroethylene-hexafluoropropylene copolymer (FEP), and is extrusion-molded so as to cover an outer periphery of the solid conductor 11. Use of the fluorine resin having low-dielectric constant increases speed of signal.

The core bundle is a twisted wire formed by twisting plural (four in the present embodiment) core wires 13 together. In the present embodiment, a ratio (P/PD) of a twisting pitch (P) of the core wire 13 to a twisted wire outer diameter (PD) is within a range of 15 to 25. The P/PD ratio is determined to be not less than 15 since the solid conductor 11 is long at the P/PD ratio of less than 15 and electrical resistance increases, leading to deterioration of electrical characteristics. Meanwhile, the P/PD ratio is determined to be not more than 25 since elasticity of the core bundle decreases at the P/PD ratio of more than 25 and a straight-advancing property of a catheter (not shown) in a blood vessel is not obtained.

The tape layer 14 is formed by spirally winding a binding tape around the outer periphery of the core bundle and has a thickness of 3 to 6 μm. The binding tape is, e.g., a resin tape of polyethylene terephthalate (PET), etc., or a paper tape.

In the present embodiment, the binding tape is wound in a direction opposite to a twisting direction of the core wire 13 (i.e., in a direction crossing the core wire 13) in order to reduce stress acting in the twisting direction of the core wire 13. This provides adequate elasticity to the catheter wire 10 and allows a straight-advancing property of a catheter (not shown) in a blood vessel to be improved.

The shield layer 15 is formed by spirally winding a conductive metal wire around the outer periphery of the tape layer 14. Preferably, a silver-plated copper wire or a silver-plated copper alloy wire is used as the metal wire. This effectively improves soldering workability at the time of terminal processing to connect an ultrasonic transducer (not shown). In addition, a winding direction of the metal wire is the same as the twisting direction of the core wire 13. This is because, if the winding direction of the metal wire is opposite to the twisting direction of the core wire 13, the metal wire is affected by stress acting in the twisting direction of the core wire 13 and becomes prone to be broken.

In the present embodiment, the metal wire constituting the shield layer 15 has a tensile strength of not less than 900 MPa and an elongation percentage of not more than 2%. This provides adequate elasticity to the catheter wire 10, and a straight-advancing property of a catheter (not shown) in a blood vessel is thus improved. In addition, the metal wire has a conductivity of not less than 80%. This decreases a signal attenuation rate and it is thus possible to obtain good electrical characteristics.

The sheath layer 16 is formed of a fluorine resin such as tetrafluoroethylene perfluoroalkyl vinyl ether copolymer (PFA) and is extrusion-molded so as to cover the outer periphery of the shield layer 15. In the present embodiment, the thickness of the sheath layer 16 is not more than 0.03 mm from the viewpoint of reduction in diameter. In addition, a melt flow rate (MFR) of the fluorine resin is not less than 35 so that good fluidity is provided at the time of extrusion molding.

The catheter wire 10 in the present embodiment configured as described above has an outer diameter of not more than 0.3 mm and allows reduction in diameter as compared to the case of using the conventional multicore cable 300 shown in FIG. 4.

Figure 2:
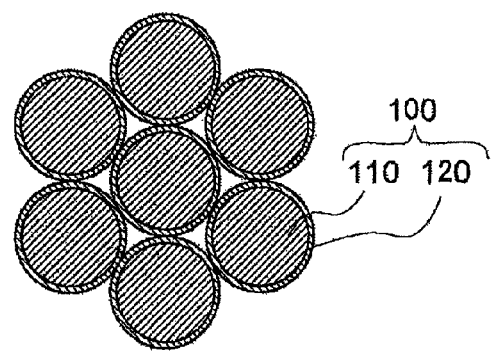
FIG. 2 is a schematic cross sectional view showing a conventional enamel wire.

Meanwhile, the structure shown in FIG. 2 in which the conventional enamel wires 100 are twisted together has a problem of unstable electrical characteristics since a shield layer is not provided and the conventional twisted wire 200 shown in FIG. 3 has a problem of unstable electrical characteristics since the signal wire 210A is separated from the ground wire 210B when being bent.

On the other hand, in the catheter wire 10 in the present embodiment, the shield layer 15 is further provided so as to cover the outer periphery of the tape layer 14 which secures the core bundle. Therefore, in the catheter wire 10 in the present embodiment, a distance between the inner conductor and the shield layer 15 does not change when being bent and it is thus possible to obtain stable electrical characteristics.

In addition, in the catheter wire 10 in the present embodiment, the solid conductor 11 constituting the core wire 13 and the metal wire constituting the shield layer 15 have a tensile strength of not less than 900 MPa and an elongation percentage of not more than 2%, and the binding tape constituting the tape layer 14 is wound in a direction opposite to the twisting direction of the core wire 13. Therefore, in the catheter wire 10 in the present embodiment, adequate elasticity is imparted to the catheter wire 10 and it is possible to improve a straight-advancing property of a catheter (not shown) in a blood vessel.

In addition, in the catheter wire 10 in the present embodiment, the solid conductor 11 constituting the core wire 13 and the metal wire constituting the shield layer 15 have a conductivity of not less than 80%. Therefore, in the catheter wire 10 in the present embodiment, a signal attenuation rate is decreased and it is thus possible to obtain good electrical characteristics.

In addition, in the catheter wire 10 in the present embodiment, the four core wires 13 constituting the core bundle are configured so that a ratio (P/PD) of a twisting pitch (P) to a twisted wire outer diameter (PD) is within a range of 15 to 25. That is, the P/PD ratio of not less than 15 prevents the solid conductor 11 from being longer than necessary and suppresses an increase in electrical resistance, on the other hand, the P/PD ratio of not more than 25 provides adequate elasticity to the core bundle. Therefore, in the catheter wire 10 in the present embodiment, it is possible to effectively improve electrical characteristics and a straight-advancing property.

In addition, in the catheter wire 10 in the present embodiment, a silver-plated wire is used as the metal wire constituting the shield layer 15 and this metal wire is wound in the same direction as the twisting direction of the core wire 13. Therefore, in the catheter wire 10 in the present embodiment, it is possible to improve soldering workability at the time of terminal processing and to effectively prevent breakage of the metal wire due to influence of stress generated in the twisting direction.

The present invention is not intended to be limited to the above-mentioned embodiment and can be appropriately modified and implemented without departing from the gist of the invention.

For example, the tensile strength, elongation percentage and conductivity of the solid conductor 11, those of the metal wire, the thickness of the tape layer 14 and that of the sheath layer 16 are not limited to the above-mentioned numerical values and can be appropriately changed to optimal numerical values depending on the intended use or technical specification.

What is claimed is:

1. A catheter wire, comprising:
   a core bundle comprising a plurality of core wires twisted in a twisting direction, each of said cores wires comprising a solid conductor covered with an insulation;
   a tape layer comprising a spirally wound binding tape wound on an outer periphery of the core bundle in a direction opposite to the twisting direction of the core wires;
   a shield layer comprising a spirally wound metal wire wound on an outer periphery of the tape layer in a same direction as the twisting direction of the core wires; and
   a sheath layer formed on an outer periphery of the shield layer,
   wherein the solid conductor and the metal wire have a tensile strength of not less than 900 MPa and an elongation percentage of not more than 2%.

2. The catheter wire according to claim 1, wherein the solid conductor and the metal wire have a conductivity of not less than 80%.

3. The catheter wire according to claim 1, wherein a ratio (P/PD) of a twisting pitch (P) of the core wire to a twisted wire outer diameter (PD) is in a range of 15 to 25.

4. The catheter wire according to claim 1, wherein the sheath layer comprises a fluorine resin having a melt flow rate (MFR) of not less than 35 g/10 min.

5. The catheter wire according to claim 1, wherein the metal wire comprises a silver-plated wire.

* * * * *